(12) United States Patent
Liu et al.

(10) Patent No.: US 8,563,245 B2
(45) Date of Patent: Oct. 22, 2013

(54) METHOD FOR CHANGING SURFACE PROPERTIES OF A SUBSTRATE FROM IMMOBILIZED BIOMOLECULES

(75) Inventors: Ming-Yu Liu, Hsinchu (TW); Yuh-Shyong Yang, Hsinchu (TW); Yen-Pei Lu, Hsinchu (TW); Chih-Heng Lin, Hsinchu (TW)

(73) Assignee: National Applied Research Laboratories, Taipei (TW)

( * ) Notice: Subject to any disclaimer, the term of this patent is extended or adjusted under 35 U.S.C. 154(b) by 0 days.

(21) Appl. No.: 13/437,340

(22) Filed: Apr. 2, 2012

(65) Prior Publication Data

US 2013/0210110 A1   Aug. 15, 2013

(30) Foreign Application Priority Data

Feb. 10, 2012   (TW) .............................. 101104498 A

(51) Int. Cl.
| | |
|---|---|
| *C12N 11/16* | (2006.01) |
| *C12N 9/00* | (2006.01) |
| *C12Q 1/68* | (2006.01) |
| *C07H 21/02* | (2006.01) |

(52) U.S. Cl.
USPC ............ 435/6.1; 435/174; 435/175; 435/181; 435/287.2; 530/350; 536/23.1

(58) Field of Classification Search
None
See application file for complete search history.

(56) References Cited

U.S. PATENT DOCUMENTS

| | | | |
|---|---|---|---|
| 7,981,632 B2 * | 7/2011 | Schmidt | ......................... 435/7.5 |
| 2004/0043384 A1 * | 3/2004 | Oleinikov | ......................... 435/6 |

* cited by examiner

*Primary Examiner* — Betty Forman
(74) *Attorney, Agent, or Firm* — Wang Law Firm, Inc.; Li K. Wang; Stephen Hsu

(57) ABSTRACT

A method that modifies surface properties of a substrate by manipulating the immobilized biomolecules in mild biological condition. The manipulation comprised steps of: providing a biomolecule combined with at least one ssDNA combined with a first protein through an affinity binding tag; adding a second ssDNA conjugated with a second protein with a concentration greater than that of the first protein; and replacing the first protein on the ssDNA with the second protein through chemical competitive principle. The invention may comprise the steps with proper design of biotinylated DNA probes, the functionalized ssDNA nanotemplates can be recovered to its unbound state through a thermodynamic principle.

5 Claims, 7 Drawing Sheets

METHOD FOR CHANGING SURFACE PROPERTIES OF A SUBSTRATE FROM IMMOBILIZED BIOMOLECULES

CROSS-REFERENCE TO RELATED APPLICATION

This application claims the benefit of Taiwan Patent Application No. 101104498 filed on Feb. 10, 2012, in the Taiwan Intellectual Property Office, the disclosure of which is incorporated herein in its entirety by reference.

BACKGROUND OF THE INVENTION

1. Field of the Invention

The present invention relates to a surface modification method, and more particularly to the method of modifying the surface properties of biomolecules and recovering the original status without any harsh treatment, such as strong basic agents, or thermal treatment (more than 37° C.). The invention can be used for functionalization, refunctionalization and rejuvenation of a substrate on a biosensor.

2. Description of Related Art

A biosensor is defined as "a device using a fixed biomolecule probe and combining a transducer and an electronic device, such that a physical signal can be generated to detect chemical matters inside or outside a living organism, after a specific interaction of the bio-molecule probe and an object to be tested takes place". For example, a bio-molecule such as an enzyme or an antigen converts a concentration of a chemical matter (such as glucose, potassium ions or cholesterol) into an electronic signal or an optical signal to measure a trace composition. Since the biosensor is usually used in clinic examinations, it has a relatively strict requirement on precision.

A specific bio-molecule probe (with deoxyribonucleic acid, protein, and etc) is fixed onto a substrate surface of the biosensor, not only functionalizing the substrate surface of the biosensor, but also providing the sensitivity and specificity for the test of the biosensor. However, once the bio-molecule probe is fixed onto the substrate surface of the biosensor and coupled to the object to be tested, it is very difficult to regenerate the bio-molecule probe to the original status before the examination takes place. Therefore, most biochips or biosensors are one-time-use disposable devices, which cannot be used repeatedly, such that the price of bio-chips or biosensors is high.

Traditionally, strong acid, strong alkali agents or a high temperature processing biomolecule probes are required to separate the object to be tested on the bio-molecule probe and resume the original un-examined status. However, these measures cause irreversible damage to the bio-molecule probe or electronic device of any biosensor while affecting the precision of the biosensor, so that the biosensor cannot be used repeatedly. In addition, the conventional method of separating an object to be tested on the bio-molecule probe is to use the strong acid, strong alkali or high temperature processing that may damage the substrate surface of the biosensor, so that another bio-molecule cannot functionalize the substrate surface again, and the biosensor cannot be used repeatedly.

In summation, the conventional method of modifying the surface of biomolecules still has the drawbacks of damaging biosensors or electronic devices, reducing the precision of the biosensor, failing to regenerate the biosensor for a repeated use, and incurring a high price, and thus requires further improvements and feasible solutions.

SUMMARY OF THE INVENTION

In view of aforementioned problems of the prior art, it is a primary objective of the invention to provide a method of modifying the surface of biomolecules to overcome the drawbacks of the conventional method of separating an object to be tested on the biomolecule probe that damages the biosensor or electronic device, fails to regenerate the biosensor, and causes low precision and high cost of the biosensor.

To achieve the foregoing objective, the present invention provides a method of modifying the surface of biomolecules, comprising the steps of: providing a bio-molecule combined with at least one single-stranded deoxyribonucleic acid (ssDNA) which is combined with a first protein by an affinity binding tag; adding a second protein having a concentration greater than that of the first protein; and replacing the first protein on at least one of the ssDNA by a second protein through a chemical competitive principle.

Preferably, the biomolecule includes a DNA probe having 18 to 3000 bases.

Preferably, at least one of the ssDNA has 15 to 35 bases.

Preferably, the first protein and the second protein are combined with the affinity binding tag on at least one of the ssDNA through an affinity tag, and a combination between the affinity tag and the affinity binding tag is a reversible combination.

Preferably, the affinity tag includes streptavidin, and the affinity binding tag includes biotin.

Preferably, the first protein and the second protein include alkaline phosphatase or horseradish peroxidase.

Preferably, the biomolecule is applied to a biochip or a biosensor.

To achieve the foregoing objective, the present invention further provides a method of modifying the surface of biomolecules, with proper design of the biotinylated DNA probes. The functionalized ssDNA nanotemplates can be recovered to its unbound state in mild biological condition, rejuvenation of the bioactive DNA nanotemplate could be achieved by removing the biotinylated DNA probes on the ssDNA nanotemplate by using a recovery DNA.

steps of: providing a bio-molecule combined with at least one first ssDNA, wherein a first free energy ($\Delta G1$) exists between at least one of the first ssDNA and the bio-molecule; adding a recovery ssDNA, wherein a second free energy ($\Delta G2$) exists between the recovery ssDNA and at least one of the first ssDNA, and the second free energy is smaller than the first free energy; and separating at least one of the first ssDNA from the biomolecule and combining at least one of the first ssDNA with the recovery ssDNA through a thermodynamic principle.

Preferably, the bio-molecule includes a DNA probe having 18 to 3000 bases.

Preferably, at least one of the first ssDNA and the second ssDNA have 15 to 35 bases.

Preferably, the first free energy and the second free energy have a negative value.

Preferably, at least one of the first ssDNA is partially complemented with the bio-molecule, and the second ssDNA is wholly complemented with at least one of the first ssDNA.

Preferably, the bio-molecule is applied in a bio-chip or a biosensor.

The method of modifying the surface of bio-molecules of the present invention can replace the original bonded object to be tested and recover the original status of the object to be tested (before it is connected) by adopting the chemical competitive principle or thermodynamic principle at room temperature without using acidic or alkaline chemicals, or can change the chemical properties of the substrate surface of the biosensor. The present invention adds a competitive matter with a higher concentration to replace the original affinity binding to achieve the effect of replacing a matter with a specific function (such as an enzyme) by a matter with the same function or another function to change the original functionality of the substrate surface, so that the original substrate surface is regenerated. On the other hand, the present invention is also applicable for the principle of complementing paired DNAs by using a thermal stable recovery DNA, so that the originally combined object to be tested and the paired double-stranded DNA to resume the original ssDNA probe to regenerate the DNA probe.

In summation, the method of modifying the surface of bio-molecules of the present invention has one or more of the following advantages:

(1) The method of modifying the surface of biomolecules of the present invention is applicable for substrate surfaces of various different biosensors and bio-chips, and users can use the same set of biosensor for testing and maintaining the precision of signals and the specificity of the object to be tested.

(2) The method of modifying the surface of biomolecules of the present invention does not require any strong acid, strong alkali or high temperature for the reaction, but the reaction can take place at room temperature, so that the substrate surface of the biosensor and the electronic device will not be damaged, and the original chemical properties of the substrate surface can be maintained.

(3) The method of modifying the surface of bio-molecules of the present invention can replace the ssDNA for more than 90%, the enzyme for more than 83%, so that the substrate surface of the biosensor can be regenerated, and the regenerated surface can be modified.

(4) The method of modifying the surface of biomolecules of the present invention can regenerate the biosensor and the biochip and modify the regenerated surface, so that the biosensor and biochip can be used repeatedly to lower the examination and fabrication cost of biosensors and biochip.

DETAILED DESCRIPTION OF THE PREFERRED EMBODIMENTS

The technical contents and characteristics of the present invention will be apparent with the detailed description of a preferred embodiment accompanied with related drawings as follows. For simplicity, same numerals are used in the following preferred embodiment to represent respective same elements.

Embodiment 1

Regeneration of the DNA Probe

Figure 1:
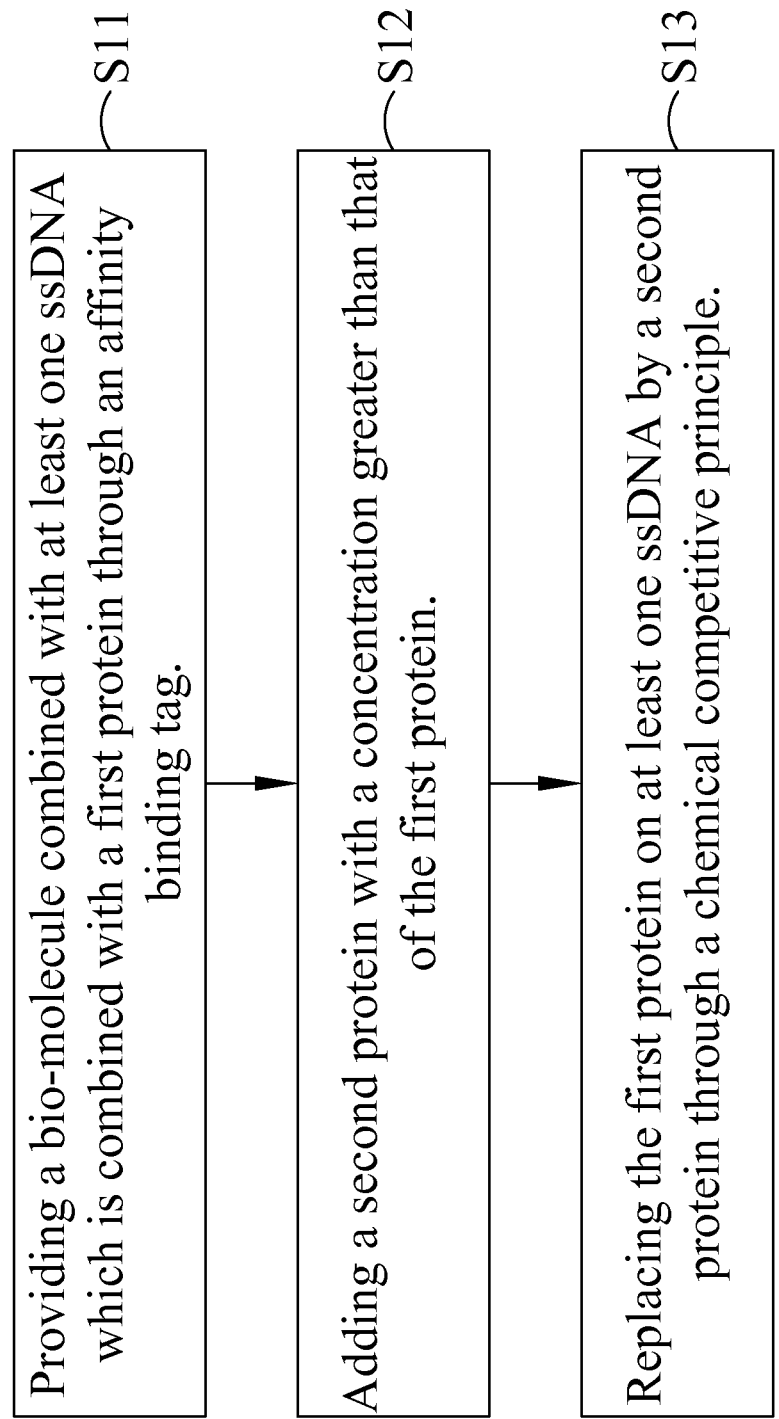
FIG. 1 is a flow chart of a method of modifying the surface of a bio-molecule probe in accordance with a first preferred embodiment of the present invention.
Figure 2:
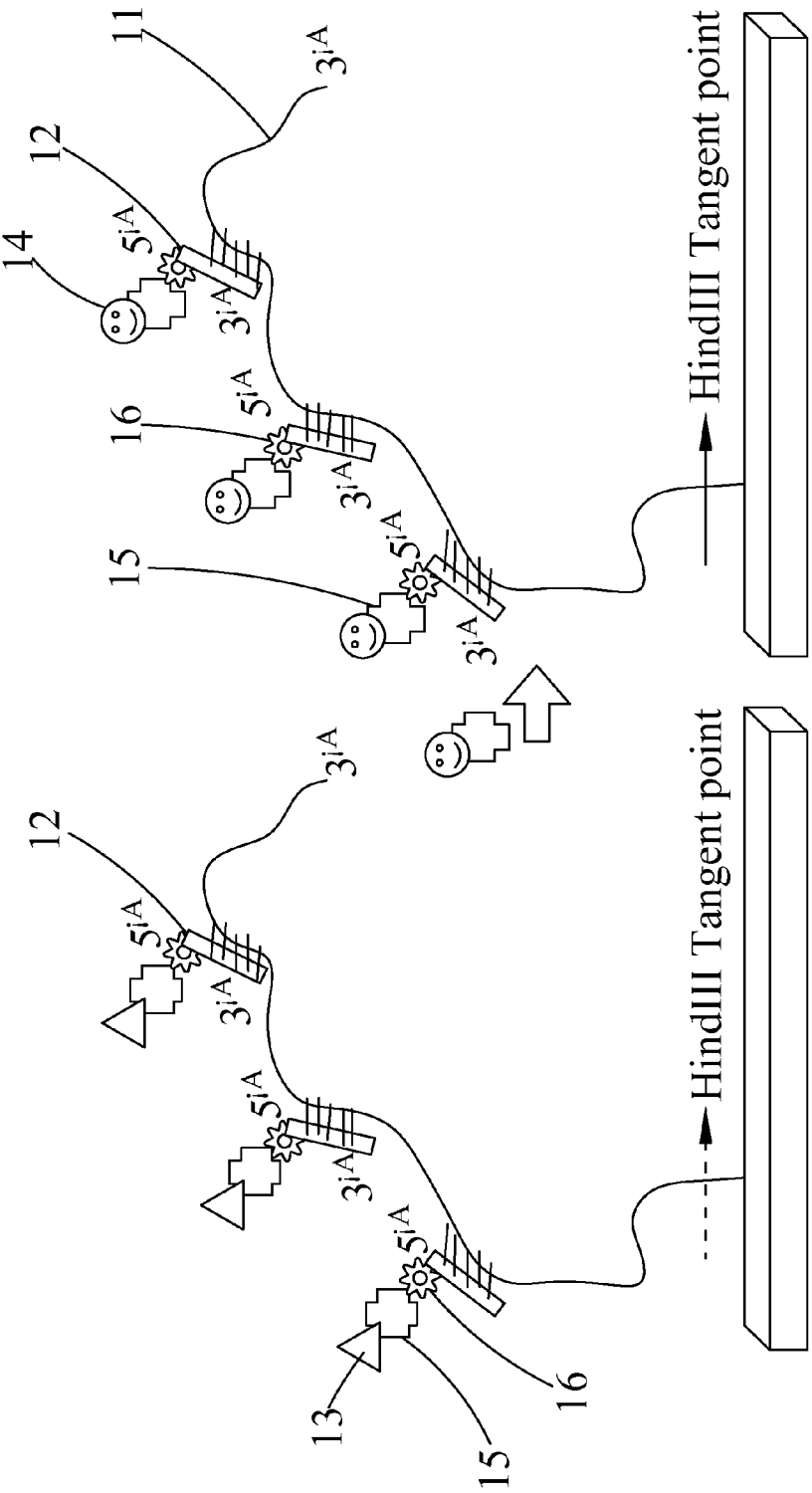
FIG. 2 is a schematic view of a method of modifying the surface of bio-molecules in accordance with the first preferred embodiment of the present invention.

With reference to FIGS. 1 and 2 for a flow chart and a schematic view of a method of modifying the surface of bio-molecules in accordance with the first preferred embodiment of the present invention respectively, the method of modifying the surface of bio-molecules comprises the following steps:

S11: Provide a bio-molecule combined with at least one ssDNA which is combined with a first protein through an affinity binding tag.

S12: Add a second protein with a concentration greater than that of the first protein.

S13: Replace the first protein on at least one ssDNA by a second protein through a chemical competitive principle.

In an example of this preferred embodiment, the bio-molecule 11 can be one selected from the collection of deoxyribonucleic acid (DNA), enzyme, antigen, receptors) and any bio-molecule applied in a biosensor or a bio-chip, and the present invention uses ssDNA as a DNA probe, and the DNA probe of the present invention has a length of 18 to 3000 bases, and preferably 500 to 2500 bases, but the invention is not limited to these numbers of bases only.

In an example of this preferred embodiment, the first protein 13 and the second protein 14 can be combined onto an affinity binding tag 16 of at least one ssDNA through an affinity tag 15, and the affinity tag 15 and the affinity binding tag 16 are paired for their use. For example, biotin-streptavidin, (His tag-Ni2+), glutathione-S-transferase tag-glutathione can be paired, and other suitable pairs of the affinity tag 15 and the affinity binding tag 16 can be used according to the experiment requirements and conditions. In this embodiment of the invention, the affinity tag 15 is streptavidin, and the affinity binding tag 16 is biotin, but the invention is not limited to such arrangement only.

Wherein, the combination of the affinity tag 15 and the affinity binding tag 16 is a reversible combination. For example Protein A and Protein B are labeled as the affinity tag 15 and the affinity binding tag 16 respectively. If the Protein A and Protein B are combined through the affinity tag 15 and the affinity binding tag 16, a high-concentration Protein C with a labeled affinity tag 15 can be used to replace the combination of Protein A and Protein B with the affinity tag 15. Now, the combination of the affinity tag 15 and the affinity binding tag 16 is a reversible combination.

In an example of this preferred embodiment, the ssDNA12 can be designed in any sequence according to the DNA probe, and the present invention adopts the ssDNA12 with the sequence identification number: 1 as an example, and biotin is modified at an end 5'.

In an example of this preferred embodiment, the first protein 13 and the second protein 14 can be enzymes, antigens, or protein of the same or different types. In this embodiment of the present invention, the first protein 13 and the second protein 14 are different enzymes, wherein the first protein 13 is alkaline phosphatase, and the second protein 14 is horseradish peroxidase. In another example of this preferred embodiment, the first protein 13 is horseradish peroxidase, and the second protein 14 is alkaline phosphatase, but the invention is not limited to these arrangements only.

In addition, the bio-molecule used in the method of modifying the surface of bio-molecules of the present invention can be applied to various bio-chips or biosensors including but not limited to blood glucose meters, lipid meters, and micro array bio-chips.

Embodiment 2

Method of Regenerating the DNA Probe

Figure 3:
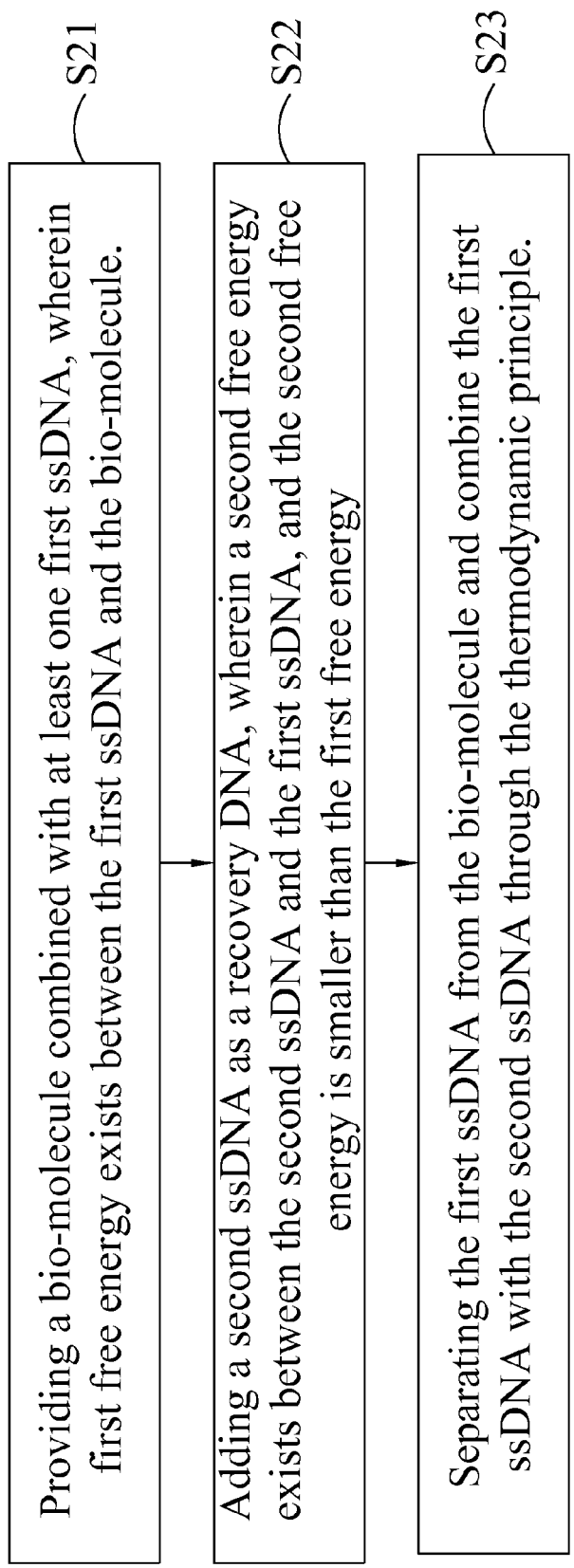
FIG. 3 is a flow chart of a method of modifying the surface of a bio-molecule probe in accordance with a second preferred embodiment of the present invention.
Figure 4:
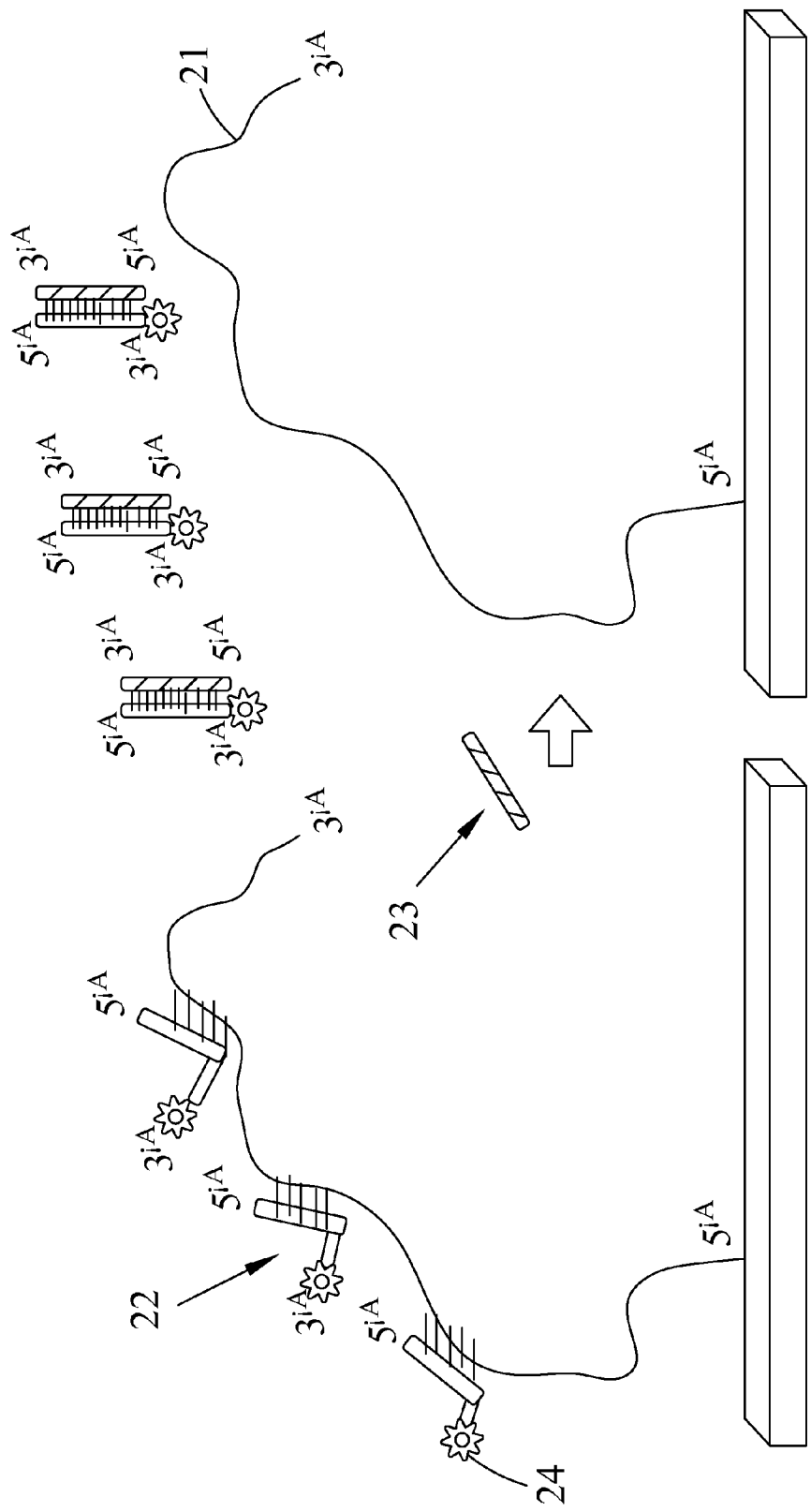
FIG. 4 is a schematic view of a method of modifying the surface of bio-molecules in accordance with the second preferred embodiment of the present invention.

With reference to FIGS. 3 and 4 for a flow chart and a schematic view of a method of modifying the surface of bio-molecules in accordance with the second preferred embodiment of the present invention respectively, the method of modifying the surface of bio-molecules comprises the following steps:

S21: Provide a bio-molecule combined with at least one first ssDNA, wherein first free energy ($\Delta G1$) exists between the first ssDNA and the bio-molecule.

S22: Add a second ssDNA, as a recovery DNA, wherein a second free energy ($\Delta G2$) exists between the second ssDNA and the first ssDNA, and the second free energy is smaller than the first free energy, S23: Separate the first ssDNA from the bio-molecule and combine the first ssDNA with the second ssDNA through the thermodynamic principle.

In an example of this preferred embodiment, the bio-molecule 21 is one selected from the collection of deoxyribonucleic acid, enzyme, antigen and any bio-molecule applied in a biosensor or a bio-chip, and this embodiment of the present invention uses the ssDNA as the DNA probe, wherein the DNA probe has a length of 18 to 3000 bases and preferably 500 to 2500 bases, but the invention is not limited to such length only.

In an example of this preferred embodiment, this embodiment uses 21 bases as an example and prevents the ssDNA from producing a first ssDNA 22 and a second ssDNA 23 having a length of 12 to 40 bases, and preferably 15 to 35 bases, wherein the first ssDNA 22 of the sequence identification number: 2 is partially complemented with the DNA probe by 15 bases close to the end 5', and 6 bases are extended from the end 3', and the first ssDNA 22 has biotin modified at the end 3'. In addition, the second ssDNA 23 of the sequence identification number: 3 is wholly complemented with the first ssDNA 22 of the sequence identification number: 2.

In an example of this preferred embodiment, the first free energy ($\Delta G1$) and the second free energy ($\Delta G2$) have a negative value. Preferably, the first free energy ($\Delta G1$) and the second free energy ($\Delta G2$) are equal to $-15.94$ kcal/mL and $-22.72$ kcal/mL respectively in this preferred embodiment.

In addition, the bio-molecules used in the method of modifying the surface of bio-molecules of the present invention can be applied to various different bio-chips or biosensors such as blood glucose meters, lipid meters, and micro-array bio-chips, but the invention is not limited to such arrangement only.

Embodiment 3

Preferred Embodiment of the Present Invention

To allow persons ordinarily skilled in the art to implement the present invention, the following preferred embodiments are used to elaborate the present invention. It is noteworthy to point out that all parameters and chemical agents used in the embodiments are provided for the purpose of illustrating the present invention, but not intended for limiting the scope of the present invention.

Regeneration of DNA Probe

Add and react the ssDNA of the sequence identification number: 1 (with the quantity of 1.3 μM and having biotin modified at the end 5') with the DNA probe, so that the ssDNA is combined with the DNA probe. Wash the compound by a phosphoric acid washing buffer. Add 150 μL of bovine serum albumin (BSA) to block the unbound area on the surface. Use 300 μL of washing buffer to rinse the compound for three times to wash away extra bovine serum albumin (BSA). Add 70 μL of streptavidin-alkaline phosphatase solution or streptavidin-horseradish peroxidase solution (5 nM), and allow the reaction to take place at 25° C. for 45 minutes, so that the alkaline phosphatase or horseradish peroxidase is connected to the DNA probe to functionalize the DNA probe. Use 300 μL of washing buffer to wash the compound for three times to wash away extra testing agent, enzyme and DNA.

Add streptavidin-horseradish peroxidase (0, 3.5, 17.5, 350 nM) or streptavidin-alkaline phosphatase (0, 7, 35, 700 nM) with different concentrations into the DNA probes connected with streptavidin-alkaline phosphatase or streptavidin-horseradish peroxidase respectively to compete for the biotin binding site, so as to replace the streptavidin-alkaline phosphatase or streptavidin-horseradish peroxidase originally combined with the DNA probe.

To confirm that the tested enzyme activity comes from the functionalized DNA probe, a tangent point of an enzyme HindIII is designed at an end where the DNA probe and the substrate surface are connected. After the enzyme HindIII is added for the reaction, the DNA probe can be removed, and then 20 units of restriction enzyme HindIII are used for the reaction taken place at 37° C. for 50 minutes to remove the DNA probe and the enzyme combined with the DNA probe.

Regeneration of the DNA Probe

Add and react the first ssDNA of the sequence identification number: 2 (with the quantity of 1.3 μM and having biotin modified at the end 3') with the DNA probe, so that the ssDNA is combined with the DNA probe.

Wash the compound by a phosphoric acid washing buffer. Add 150 μL of bovine serum albumin (BSA) to perform a blocking. Use 300 μL of washing buffer to rinse the compound for three times to wash away extra bovine serum albumin (BSA). Add 70 μL of streptavidin-horseradish peroxidase, so that the streptavidin-horseradish peroxidase is combined with the DNA probe through the biotin of the first ssDNA to functionalize the DNA probe, and use it as an indication of a separation from the first ssDNA probe.

In order to remove the first ssDNA probe from the DNA probe and regenerate the DNA probe, a second ssDNA (sequence identification number: 3) wholly complemented with the first ssDNA is designed, and 100 μL of the second ssDNA (0, 1, 2, 3 μM) with different concentrations are added to allow a reaction to take place at 37° C. for 60 minutes to complete with the DNA probe and combined with the first ssDNA.

Testing the Enzyme Activity

After the functionalized DNA probe is washed by 300 μL of the washing buffer, the enzyme activity is tested. When the activity of the horseradish peroxidase is tested, 150 μL of tetramethylbenzidine solution are added. After an incubation takes place at 25° C. for 10 minutes, the 100 μL of reacted tetramethylbenzidine solution is removed and added into a 96-well microtiter plate, and a Victor multilabel counter (by Perkin-Elmer Life Science, Inc.; USA) is used to measure the light absorbance value of the wavelength 650 nm. When the activity of the alkaline phosphatase is measured, 150 μL of P-nitrophenyl phosphate (Sigma) are added. After incubation has taken place at 25° C. for 30 minutes, the Victor multilabel counter is used to measure the light absorbance value of the wavelength 405 nm.

Experiment Results

1. Generation of the DNA Probe

Figure 5A:
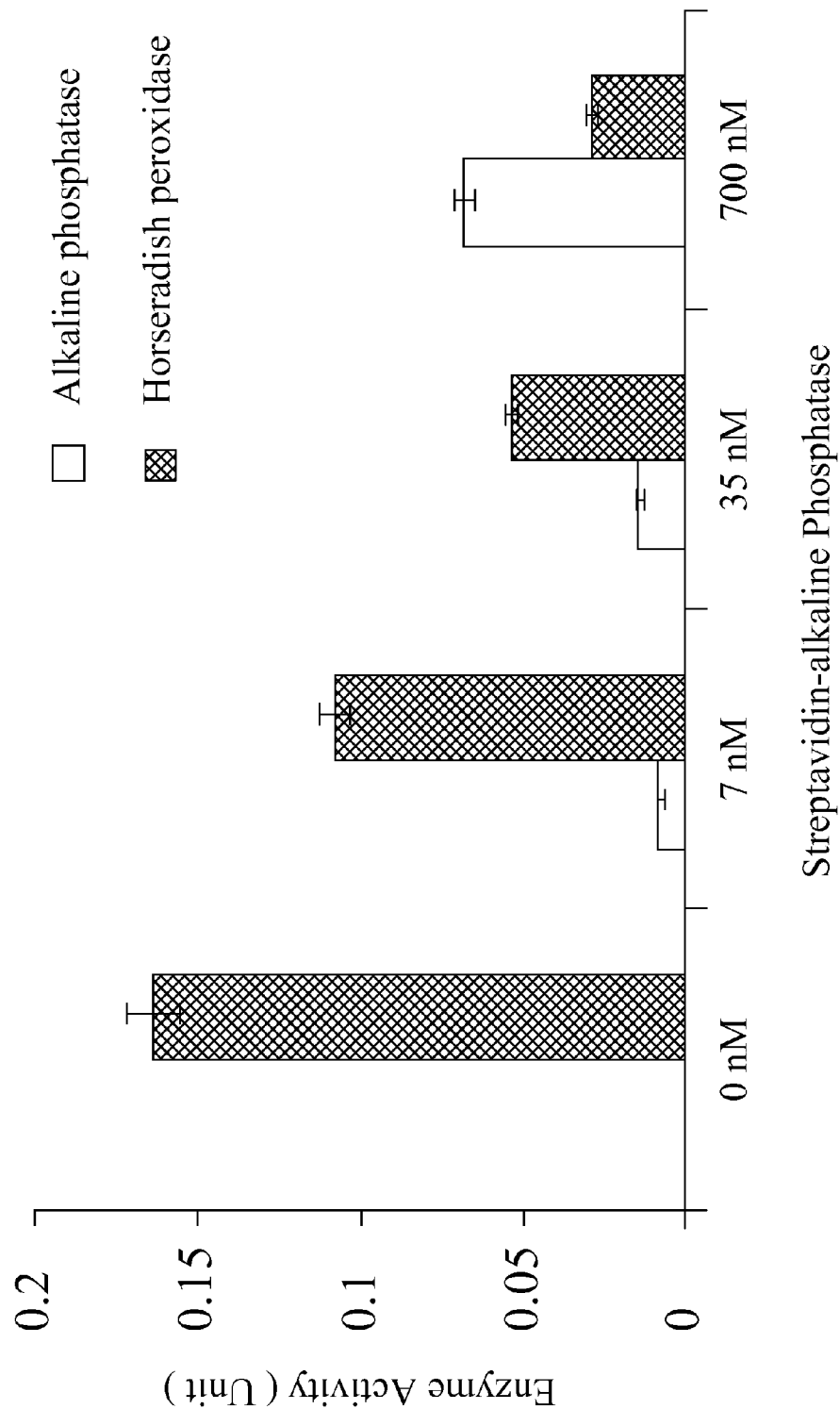
FIG. 5A is an enzyme activity graph of a first example of a method of modifying the surface of bio-molecules in accordance with a first preferred embodiment of the present invention.
Figure 5B:
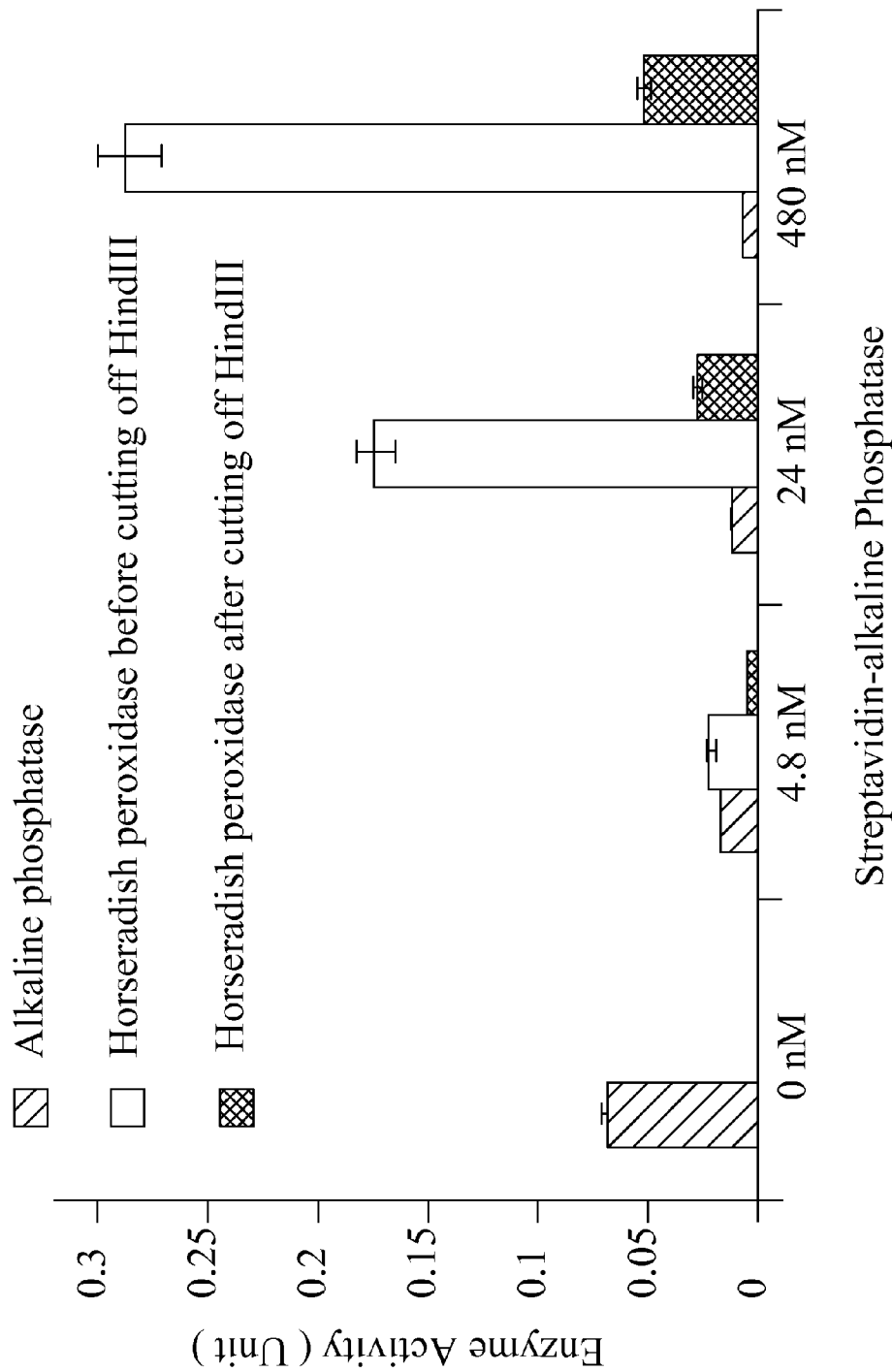
FIG. 5B is an enzyme activity graph of a second example of a method of modifying the surface of bio-molecules in accordance with the first preferred embodiment of the present invention.

With reference to FIGS. 5A and 5B for enzyme activity graphs of the first and second examples of a method of modifying the surface of bio-molecules in accordance with the first preferred embodiment of the present invention respectively, FIG. 5A shows that the functionalized DNA probe with the horseradish peroxidase combined with the streptavidin-horseradish peroxidase on the DNA probe is gradually replaced by the streptavidin-alkaline phosphatase. More specifically, under the competition of 700 nM of streptavidin-alkaline phosphatase, approximately 83% of the streptavidin-horseradish peroxidase combined with the DNA probe are gradually replaced by the streptavidin-alkaline phosphatase. In other words, the original 0.81 mU (1.63 fmole) of horseradish peroxidase is combined with the DNA probe. After alkaline phosphatase is added, approximately 0.05 mU (0.17 fmole) of alkaline phosphatase replaces the horseradish peroxidase and combines with the DNA probe. Further, alkaline phosphatase with different concentrations is added for the competition, the measured horseradish peroxidase enzyme activity is reduced gradually by the concentration dependent method, and the alkaline phosphatase enzyme activity is gradually increased by the concentration dependent method. In other words, the streptavidin-alkaline phosphatase and the streptavidin-horseradish peroxidase compete with each other to combine with the labeled biotin of the ssDNA.

Similarly, the original functionalized DNA probe with the alkaline phosphatase combined with the streptavidin-alkaline phosphatase on the DNA probe is gradually replaced by streptavidin-horseradish peroxidase as shown in FIG. 5B. More specifically, after 350 nM of streptavidin-alkaline phosphatase are added for the competition, approximately 88% of streptavidin-alkaline phosphatase combined onto the DNA probe is replaced by the streptavidin-horseradish peroxidase. In other words, the original 0.04 mU (0.15 fmole) of alkaline phosphatase is combined onto the DNA probe. After the horseradish peroxidase is added, approximately 1.71 mU (3.43 fmole) of horseradish peroxidase replaces the alkaline phosphatase and combines onto the DNA probe. After the horseradish peroxidase of different concentrations is added for the competition, the measured alkaline phosphatase enzyme activity is gradually reduced by the concentration dependent method, and the horseradish peroxidase enzyme activity is gradually increased by the concentration dependent method. In other words, streptavidin-alkaline phosphatase and streptavidin-horseradish peroxidase compete with each other and combine with the biotin labeled on the ssDNA.

In FIG. 5B, the restriction enzyme HindIII is added to cut off the DNA probe in order to confirm that the measured enzyme activity comes from the enzyme combined to the DNA probe. After the HindIII is added to cut off the DNA probe, the originally measured horseradish peroxidase enzyme activity is almost eliminated, indicating that the measured horseradish peroxidase activity comes from the horseradish peroxidase combined with the DNA probe.

2. Regeneration of the DNA Probe

Figure 6:
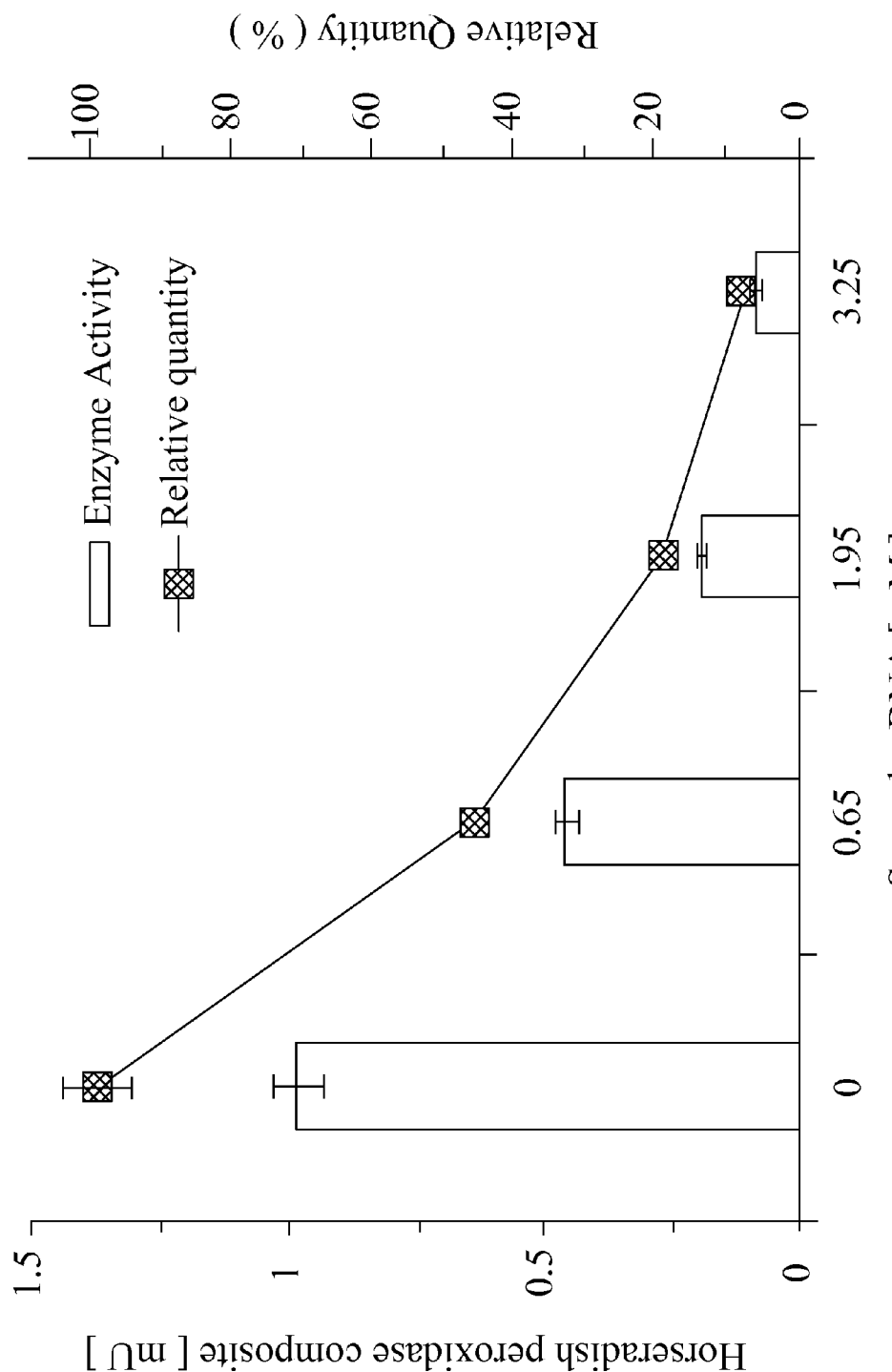
FIG. 6 is an enzyme activity graph of a method of modifying the surface of bio-molecules in accordance with a second preferred embodiment of the present invention.

With reference to FIG. 6 for an enzyme activity graph of a method of modifying the surface of bio-molecules in accordance with a second preferred embodiment of the present invention, the measured horseradish peroxidase enzyme activity of the DNA probe becomes increasingly smaller as the concentration of the added second ssDNA increases. In the other words, the first ssDNA having the horseradish peroxidase enzyme activity and originally combined with the DNA probe is separated from the DNA probe, after the second ssDNA is added. More specifically, the first ssDNA and the DNA probe have a first free energy ($\Delta G1$) −15.94 kcal/mL, and the first ssDNA and the second ssDNA have a second free energy ($\Delta G2$) −22.72 kcal/mL. According to the thermodynamic principle, the first ssDNA tends to combine with the second ssDNA and separate from the DNA probe, so that the measured horseradish peroxidase enzyme activity of the DNA probe becomes gradually less and less.

In summation of the description above, the present invention breaks through the prior art to achieve the expected objectives and complies with the patent application requirements, and thus is duly filed for patent application.

What is claimed is:

1. A method of modifying a surface of a substrate with bio-molecules, comprising the steps of:
   providing a DNA probe, having 18 to 3000 bases of repeated sequences, immobilized on a substrate, wherein each of a plurality of affinity binding tags is attached to the DNA probe via single-strained deoxyribonucleic acid (ssDNA) being complementary to each of the repeated sequences and conjugated to each of the plurality of affinity binding tags, and a plurality of first proteins which respectively conjugated to an affinity tag is attached to the DNA probe through an interaction between the affinity binding tag and the affinity tag in a reversible manner;
   adding a plurality of second proteins, respectively conjugated with the same affinity tag as that of the first proteins, with a concentration greater than that of the first protein; and
   replacing the first protein attached to the DNA probe with the second protein through a competition.

2. The method of modifying the surface of a substrate with bio-molecules as recited in claim 1, wherein the ssDNA has 15 to 35 bases.

3. The method of modifying the surface of a substrate with bio-molecules as recited in claim 1, wherein the affinity tag includes streptavidin, and the affinity binding tag includes biotin.

4. The method of modifying the surface of a substrate with bio-molecules as recited in claim 3, wherein the first protein and the second protein include an alkaline phosphatase or a horseradish peroxidase.

5. The method of modifying the surface of a substrate with bio-molecules as recited in claim 1, wherein the the substrate is a biochip or a biosensor.

* * * * *

UNITED STATES PATENT AND TRADEMARK OFFICE
CERTIFICATE OF CORRECTION

PATENT NO.        : 8,563,245 B2
APPLICATION NO.   : 13/437340
DATED             : October 22, 2013
INVENTOR(S)       : Ming-Yu Lin et al.

It is certified that error appears in the above-identified patent and that said Letters Patent is hereby corrected as shown below:

On the Title Page

Item 12, "Liu et al." should read "Lin et al."

Item 75, line 1, inventor, "Ming-Yu Liu" should read "Ming-Yu Lin"

Signed and Sealed this
Thirty-first Day of December, 2013

Margaret A. Focarino
*Commissioner for Patents of the United States Patent and Trademark Office*